United States Patent
Liu et al.

(10) Patent No.: US 12,228,549 B2
(45) Date of Patent: Feb. 18, 2025

(54) ACOUSTIC FIELD DIFFUSION TYPE ELECTROMAGNETIC ACOUSTIC TRANSDUCER WITH IMPROVED PERIODIC PERMANENT MAGNETS

(71) Applicant: Beijing University of Technology, Beijing (CN)

(72) Inventors: Zenghua Liu, Beijing (CN); Wenshuo Jiang, Beijing (CN); Zhaojing Lu, Beijing (CN); Yanhong Guo, Beijing (CN)

(73) Assignee: Beijing University of Technology, Beijing (CN)

( * ) Notice: Subject to any disclaimer, the term of this patent is extended or adjusted under 35 U.S.C. 154(b) by 288 days.

(21) Appl. No.: 17/966,175

(22) Filed: Oct. 14, 2022

(65) Prior Publication Data
US 2023/0314385 A1    Oct. 5, 2023

(30) Foreign Application Priority Data
Apr. 5, 2022   (CN) .......................... 202210352556.1

(51) Int. Cl.
| | | |
|---|---|---|
| *G01N 29/24* | (2006.01) | |
| *G01N 29/04* | (2006.01) | |
| *G01N 33/2045* | (2019.01) | |

(52) U.S. Cl.
CPC ............. *G01N 29/24* (2013.01); *G01N 29/04* (2013.01); *G01N 33/2045* (2019.01); *G01N 2291/0234* (2013.01); *G01N 2291/0289* (2013.01); *G01N 2291/101* (2013.01)

(58) Field of Classification Search
CPC .. G01N 29/00; G01N 29/04; G01N 29/22–26; G01N 22/2045; G01N 2291/0234; G01N 2291/0289; G01N 2291/101
See application file for complete search history.

(56) References Cited

U.S. PATENT DOCUMENTS

| | | | | |
|---|---|---|---|---|
| 4,434,663 A | * | 3/1984 | Peterson ............ | G01N 29/2412 73/643 |
| 7,165,453 B2 | * | 1/2007 | Flora .................... | G01N 29/221 73/643 |
| 10,502,714 B2 | * | 12/2019 | Ren .................... | G01N 29/2412 |

* cited by examiner

*Primary Examiner* — Nguyen Q. Ha
(74) *Attorney, Agent, or Firm* — Foley & Lardner LLP

(57) ABSTRACT

An acoustic field diffusion type electromagnetic acoustic transducer with improved periodic permanent magnets is provided, which includes periodic permanent magnets, a transducer framework, improved racetrack shaped coils and a transducer connector.

4 Claims, 2 Drawing Sheets

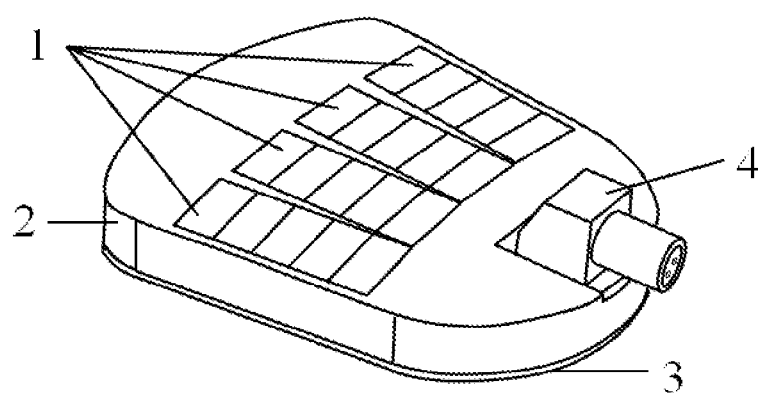
FIG. 1
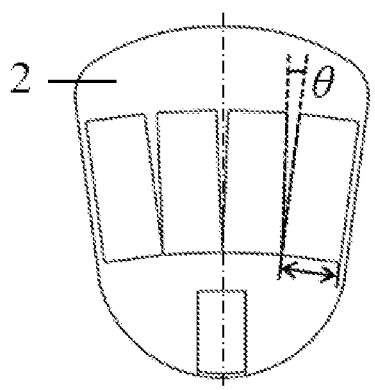 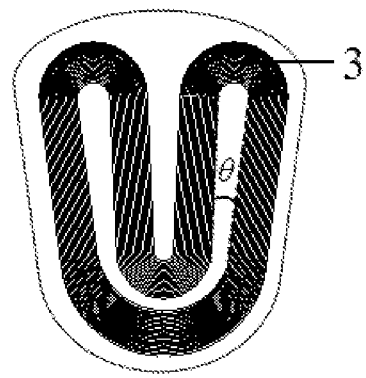
FIG. 2A    FIG. 2B
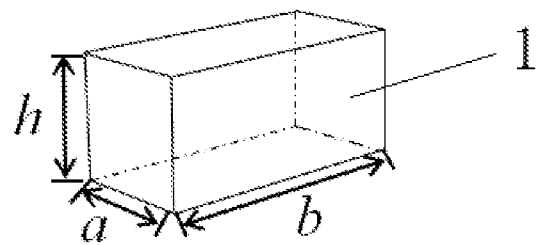
FIG. 3

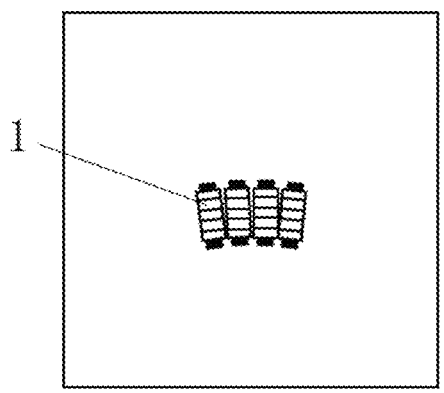
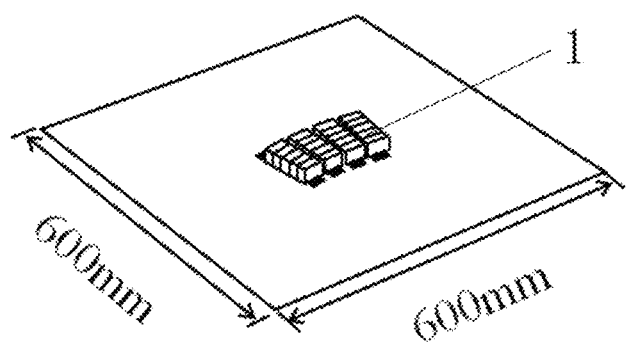
FIG. 4A  FIG. 4B
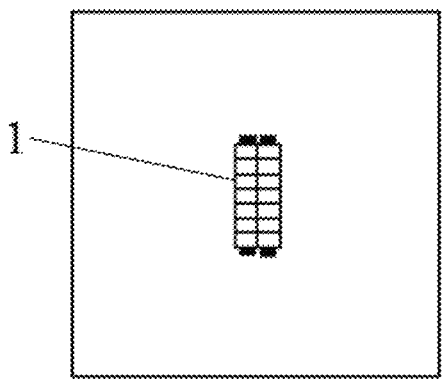
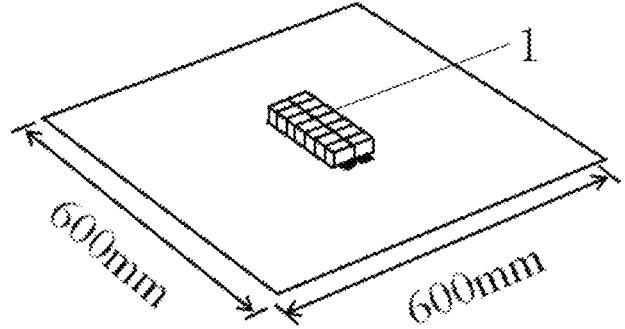
FIG. 5A  FIG. 5B
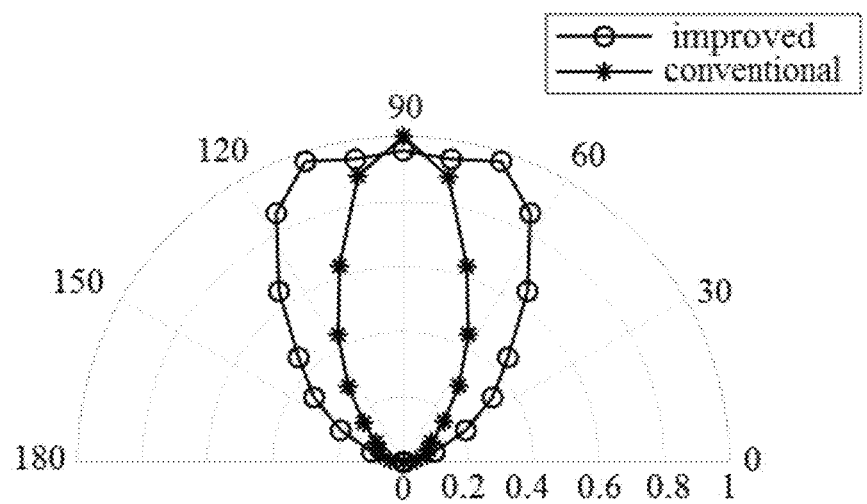
FIG. 6

ACOUSTIC FIELD DIFFUSION TYPE ELECTROMAGNETIC ACOUSTIC TRANSDUCER WITH IMPROVED PERIODIC PERMANENT MAGNETS

CROSS REFERENCE TO RELATED APPLICATION

This patent application claims the benefit and priority of Chinese Patent Application No. 202210352556.1, entitled "ACOUSTIC FIELD DIFFUSION TYPE ELECTROMAGNETIC ACOUSTIC TRANSDUCER WITH IMPROVED PERIODIC PERMANENT MAGNETS" filed on Apr. 5, 2022, the disclosure of which is incorporated by reference herein in its entirety as part of the present disclosure.

TECHNICAL FIELD

The present disclosure relates to an acoustic field diffusion type electromagnetic acoustic transducer with improved periodic permanent magnets so as to detect thin-wall metal tubular structures, and belongs to the field of ultrasonic non-destructive detection technology. Since the acoustic field of the ultrasonic guided waves excited by the transducer is diffused, the radiation range of the acoustic field is larger than that of the conventional electromagnetic acoustic transducer with periodic permanent magnets, and the detection range on defects of the thin-wall metal tubular structures is improved.

BACKGROUND

A thin-wall metal tubular structure is a common structural form in production life at present. And, this structure is usually designed for a storage structural member such as an oil gas pipeline and a storage tank, or is designed for a support structural member such as a suspension arm. These structural members are often in service in different working conditions, and are prone to generate defects such as cracks and corrosion or processing defects, which are generated during the production and manufacturing process. The existence of such defects may greatly reduce the strength of the structural members, and may cause the failure of the structural members during their use, thereby causing an accident. Therefore, it is particularly important to perform effective detection on the structural members. Currently, common non-destructive testing methods mainly include: a visual method, a ray detection technology, an ultrasonic detection technology, a magnetic powder detection technology, a penetrant detection technology, and an electromagnetic detection technology. For a thin-wall metal tubular structure, the cross-sectional dimension of the structural member is relatively large, and the length of the structural member is ranged from generally several meters to dozens of meters. For the detection on a large-size thin-walled metallic tubular structure, the above described conventional detection methods are difficult to apply. The ultrasonic guided waves can be better applied to such the thin-wall metal tubular structure due to the advantage of small attenuation and long propagation distance of ultrasonic guided waves.

At present, among transducers used for exciting and receiving ultrasonic guided waves, an electromagnetic acoustic transducer is widely concerned because of their advantages of easy mode control and no coupling. As one of the electromagnetic acoustic transducers that can excite the guided waves mode $SH_0$, the conventional electromagnetic acoustic transducer with periodic permanent magnets can excite the single $SH_0$ mode in a thin-walled metal tubular structure. But, the acoustic field is relatively concentrated, which is not conducive to scanning the defects over a large area. In order to better realize wide-range scanning of the defects in the thin-wall metal tubular structure, it is necessary to improve the conventional electromagnetic acoustic transducer with periodic permanent magnets to increase the radiation range of the acoustic field of the transducer and make the energy more uniformly distributed.

SUMMARY

The present disclosure increases a radiation range of an acoustic field at one side of the transducer by improving the distribution of the magnets in an electromagnetic acoustic transducer with periodic permanent magnets and adjusting an inclined angle between every two adjacent groups of the magnets, thereby increasing a detection range on the defects and making the energy of the transducer more uniformly distributed.

The embodiments aim to provide an acoustic field diffusion type electromagnetic acoustic transducer with improved periodic permanent magnets. In view of the problem of the acoustic field directionality of the conventional electromagnetic acoustic transducer with periodic permanent magnets, the present disclosure starts from the structural design of the transducer, increases the number of columns of magnets and adjusts an inclined angle between every two adjacent groups of the magnets (coils) to increase a radiation range of the acoustic field on one side of the transducer, thereby increasing the detection range on defects.

In order to achieve the described object, some embodiments adopt the following design solution.

An acoustic field diffusion type electromagnetic acoustic transducer with improved periodic permanent magnets, includes multiple groups of periodic permanent magnets 1, a transducer framework 2, improved racetrack shaped coils 3 and a transducer connector 4. Each group of the multiple groups of periodic permanent magnets 1 is arranged in a corresponding one of grooves of the transducer framework 2. A predetermined inclined angle is formed between every two adjacent grooves of the grooves. The improved racetrack shaped coils are arranged right below the transducer framework 2 and connected with the transducer connector 4. Each of the improved racetrack shaped coils corresponds to a corresponding one group of the multiple groups of periodic permanent magnets. The transducer connector 4 is fixed on the transducer framework 2. Multiple groups of the periodic permanent magnets 1 are arranged in grooves in the transducer framework 2, and a predetermined inclined angle is formed between every adjacent two of the grooves, so as to provide the multiple groups of periodic magnetic fields every adjacent two of which are distributed with predetermined inclined angles therebetween. The improved racetrack shaped coils are arranged right below the transducer framework 2 and are connected with the transducer connector 4, and each of the improved racetrack shaped coils corresponds to a corresponding group of the multiple groups of the periodic permanent magnets. By introducing an alternating current with a predetermined frequency into the transducer connector, the improved racetrack shaped coils can induce the induced eddy current fields on a surface of a metal piece to be tested directly below the coils, and each field has the opposite direction and the same frequency with respect to the current of the corresponding coil and is distributed with a predetermined inclined angle. Under the interaction of the periodic magnetic fields with the predetermined inclined angles and the induced eddy current fields, a Lorentz force field distributed with predetermined inclined angle is generated on the surface of the metal piece to be tested. Under the action of the Lorentz force, a periodic vibration is generated on the surface of the metal piece to be tested, so that ultrasonic waves are excited in the metal piece. Since the Lorentz force field generated by the acoustic field diffusion type electromagnetic acoustic transducer with improved periodic permanent magnets is distributed with the predetermined inclined angle, the acoustic field excited by the transducer is in a diffusion form, and has a larger radiation range compared with the acoustic field of the conventional electromagnetic acoustic transducer with the periodic permanent magnets.

According to the acoustic field diffusion type electromagnetic acoustic transducer with improved periodic permanent magnets, the predetermined inclined angle between the every two adjacent grooves in the transducer framework 2 may be denoted by θ.

According to the acoustic field diffusion type electromagnetic acoustic transducer with improved periodic permanent magnets, an included angle between every two adjacent racetrack shaped coils of the improved racetrack shaped coils 3 may be denoted by θ, and current directions on the every two adjacent racetrack shaped coils may be opposite.

According to the acoustic field diffusion type electromagnetic acoustic transducer with improved periodic permanent magnets, a width a of a magnet of the periodic permanent magnets 1 may be equal to half of a wavelength of targeted excited guided waves, i.e., shear horizontal mode $SH_0$.

The embodiments can achieve the following beneficial effects.
  1. The formation of both the predetermined inclined angle between every two adjacent groups of magnets and the predetermined inclined angle between every two adjacent coils makes the acoustic field generated on one side of the transducer more dispersed, thereby expanding the detection range on the defects.
  2. The multiple racetrack shaped coils and the multiple groups of periodic permanent magnets can increase the signal strength of the transducer, and can make the energy for generating the acoustic field more uniformly distributed.

BRIEF DESCRIPTION OF THE DRAWINGS

FIG. 1 is a schematic structural diagram of an acoustic field diffusion type electromagnetic acoustic transducer with improved periodic permanent magnets.

FIG. 2A is a schematic diagram of a transducer framework.

FIG. 2B is a schematic diagram of an excitation coil.

FIG. 3 is a schematic diagram of a permanent magnet.

FIG. 4A is a top view of a model of the acoustic field diffusion type electromagnetic acoustic transducer with improved periodic permanent magnets.

FIG. 4B is a perspective view of the model of the acoustic field diffusion type electromagnetic acoustic transducer with improved periodic permanent magnets.

FIG. 5A is a top view of a model of a conventional electromagnetic acoustic transducer with periodic permanent magnets.

FIG. 5B is a perspective view of a model of a conventional electromagnetic acoustic transducer with periodic permanent magnets.

FIG. 6 is a comparison diagram of the acoustic field distribution of two transducers.

List of the characters reference: 1 periodic permanent magnet; 2 transducer framework; 3 excitation coil; and 4 transducer connector.

DETAILED DESCRIPTION OF THE EMBODIMENTS

The present disclosure will be further described below in combination with the drawings and embodiments, and the following embodiments are merely descriptive rather than restrictive, and shall not be used to limit the scope of protection of the present disclosure.

A schematic structural view of an acoustic field diffusion type electromagnetic acoustic transducer with improved periodic permanent magnets is shown in FIG. 1. The acoustic field diffusion type electromagnetic acoustic transducer with improved periodic permanent magnets includes periodic permanent magnets 1, a transducer framework 2 and improved racetrack shaped coils 3. The effect of the acoustic field diffusion type electromagnetic acoustic transducer with improved periodic permanent magnets is analyzed by establishing a finite element simulation model. A simulation model of the acoustic field diffusion type electromagnetic acoustic transducer with improved periodic permanent magnets is simplified as shown in FIG. 4A and FIG. 4B. A magnet is sized to have a height h of 10 mm, a length b of 15 mm, a width a of 7 mm, and an inclined angle θ with a value equal to 2.5 degrees. The acoustic field diffusion type electromagnetic acoustic transducer with improved periodic permanent magnets is provided with four columns of periodic permanent magnets in total, and each column of periodic magnets includes five permanent magnets in total. Magnetic poles of every two adjacent permanent magnets of the each column of the periodic magnets are opposite. An inclined angle θ between every two adjacent columns of periodic permanent magnets is 2.5 degrees. An angle θ between every two adjacent coils is 2.5 degrees, and the coils are arranged below the magnets. In order to facilitate observing improvement effects, a simulation model of a conventional electromagnetic acoustic transducer with periodic permanent magnets is constructed as FIG. 5A and FIG. 5B. A magnet is sized to have a height h of 10 mm, a length b of 15 mm and a width a of 7 mm. The conventional electromagnetic acoustic transducer is provided with two columns of periodic permanent magnets, and the magnets (coils) are parallel to each other without an inclined angle. Each of the acoustic field diffusion type electromagnetic acoustic transducer with improved periodic permanent magnets in the present disclosure and the conventional electromagnetic acoustic transducer with periodic permanent magnets are arranged on a steel plate with a specification of 600 mm×600 mm×4 mm. A sinusoidal signal modulated by a Hanning function with a central frequency of f=220 kHz and an amplitude of 1 A is introduced into the coils, and currents on every two adjacent racetrack shaped coils are opposite. By acquiring the maximum value of an amplitude of a direct wave at a half circle 100 mm away from a center of the transducer, two effects of the acoustic field diffusion type electromagnetic acoustic transducer with improved periodic permanent magnets and the conventional electromagnetic acoustic transducer with periodic permanent magnets are compared.

FIG. 6 shows results of the orientation of the acoustic fields of the acoustic field diffusion type electromagnetic acoustic transducer with improved periodic permanent magnets and the conventional electromagnetic acoustic transducer with periodic permanent magnets. It can be clearly seen from the results that the radiation range of the acoustic field of the conventional electromagnetic acoustic transducer with periodic permanent magnets is within ±20 degrees with respect to the center of this transducer, and the acoustic field of the conventional electromagnetic acoustic transducer is concentrated. The radiation range of the acoustic field of the acoustic field diffusion type electromagnetic acoustic transducer with improved periodic permanent magnets is within ±30 degrees with respect to the center of the transducer, the radiation range of the acoustic field of the acoustic field diffusion type electromagnetic acoustic transducer with periodic permanent magnets is larger, and its energy is more uniformly distributed. It shows that the detection range of the acoustic field diffusion type electromagnetic acoustic transducer with improved periodic permanent magnets is larger than that of the conventional electromagnetic acoustic transducer with periodic permanent magnets.

An acoustic field diffusion type electromagnetic acoustic transducer with improved periodic permanent magnets designed in the present disclosure is provided. The following arrangement of coils and multiple groups of periodic permanent magnets is adopted: every adjacent two of the magnets (coils) are provided with a predetermined inclined angle therebetween. So, the radiation range of the acoustic field of the transducer is increased, the energy thereof is more uniformly distributed, and the scanning range of the transducer is increased. Compared with the conventional electromagnetic acoustic transducer with periodic permanent magnet, it can be seen that the radiation range of the acoustic field of the acoustic field diffusion type electromagnetic acoustic transducer with improved periodic permanent magnets is larger than that of the conventional electromagnetic acoustic transducer with periodic permanent magnets, and the energy is more uniformly distributed, which indicates that the scanning range and the detection capability of the acoustic field diffusion type electromagnetic acoustic transducer with improved periodic permanent magnets are enhanced.

What is claimed is:

1. An acoustic field diffusion type electromagnetic acoustic transducer with improved periodic permanent magnets, comprising:

a plurality of groups of periodic permanent magnets, a transducer framework, and improved racetrack shaped coils and a transducer connector;

wherein each group of the plurality of groups of periodic permanent magnets is arranged in a corresponding one of grooves of the transducer framework, a predetermined inclined angle is formed between every two adjacent grooves of the grooves, the improved racetrack shaped coils are arranged right below the transducer framework and are connected with the transducer connector, each of the improved racetrack shaped coils corresponds to a corresponding one group of the plurality of groups of periodic permanent magnets, and the transducer connector is fixed on the transducer framework; and wherein a width of a magnet of the plurality of groups of periodic permanent magnets is equal to half of a wavelength of targeted excited guided waves of shear horizontal mode $SH_0$.

2. The acoustic field diffusion type electromagnetic acoustic transducer with improved periodic permanent magnets according to claim 1, wherein the predetermined inclined angle between the every two adjacent grooves in the transducer framework is denoted by θ, a value of which is equal to 2.5 degrees.

3. The acoustic field diffusion type electromagnetic acoustic transducer with improved periodic permanent magnets according to claim 1, wherein an included angle between every two adjacent racetrack shaped coils of the improved racetrack shaped coils is denoted by θ, and current directions on the every two adjacent racetrack shaped coils are opposite.

4. The acoustic field diffusion type electromagnetic acoustic transducer with improved periodic permanent magnets according to claim 1, wherein a magnetizing direction of each magnet of the plurality of groups of periodic permanent magnets is a thickness direction of the magnet, and magnetic pole directions of every two adjacent magnets of the each group of the plurality of groups periodic permanent magnets are opposite.

* * * * *